US006872543B1

United States Patent
Sipponen et al.

(10) Patent No.: US 6,872,543 B1
(45) Date of Patent: Mar. 29, 2005

(54) METHOD FOR ASSESSING THE RISK OF PEPTIC ULCER, COMPRISING THE STEPS OF DETERMINING QUANTITATIVELY THE CONCENTRATIONS OF PEPSINOGEN I (PGI) AND GASTRIN-17 IN A SERUM SAMPLE

(75) Inventors: Pentti Sipponen, Espoo (FI); Matti Härkönen, Espoo (FI); Osmo Suovaniemi, Helsinki (FI); Erik Forsblom, Espoo (FI)

(73) Assignee: Biohit Oyj, Helsinki (FI)

( * ) Notice: Subject to any disclaimer, the term of this patent is extended or adjusted under 35 U.S.C. 154(b) by 0 days.

(21) Appl. No.: 09/959,551

(22) PCT Filed: Apr. 28, 2000

(86) PCT No.: PCT/FI00/00377

§ 371 (c)(1),
(2), (4) Date: Jan. 16, 2002

(87) PCT Pub. No.: WO00/67035

PCT Pub. Date: Nov. 9, 2000

(30) Foreign Application Priority Data

Apr. 30, 1999 (FI) .................................................. 990992

(51) Int. Cl.[7] .......................................... G01N 33/573
(52) U.S. Cl. ...................... 435/7.32; 435/7.23; 435/4; 435/7.1; 435/7.4; 435/7.7; 435/7.72; 435/7.91; 435/6; 435/252.3; 530/388.1; 530/388.4; 530/388.7; 530/350; 530/387.1
(58) Field of Search .............................. 435/7.32, 4, 6, 435/12, 7.1, 7.4, 7.21, 254.11, 69.1, 7.35, 7.37, 7.92, 7.93, 7.94, 71.2, 7.22, 7.2, 7.31, 7.34, 243, 252.3, 7.23, 7.7, 7.72, 7.91; 436/900, 501, 527, 512, 68, 540, 598, 530; 600/300, 532, 543; 800/9, 3; 530/350, 388.7, 387.1, 388.4, 388.3

(56) References Cited

U.S. PATENT DOCUMENTS 6,156,525 A * 12/2000 Furuta ........................ 435/7.4

FOREIGN PATENT DOCUMENTS

| WO | 9615456 | 5/1996 |
| WO | 96/15456 | * 5/1996 |

OTHER PUBLICATIONS

Ardrill, J et al, Regulatory Peptides, 1992, vol. 40(2), Jul. 23, p. P109, abstract only.*

Chen, Tseng–Shing et al, The American Joural of Gastroenterology, vol. 89(9), pp. 1511–1514, 1994.*

Hallissey, MT et al, Scandinavian Journal of GAstroenterology, vol. 29(12), pp. 1129–1134, Dec. 1994.*

(Continued)

Primary Examiner—Lynette R. F. Smith
Assistant Examiner—Ginny Allen Portner
(74) Attorney, Agent, or Firm—Birch, Stewart, Kolasch & Birch, LLP

(57) ABSTRACT

The present invention concerns a method for assessing the risk of peptic ulcer by determining the presence and topographic phenotype of gastritis in an individual, by determining quantitatively the pepsinogen I and gastin-17 concentrations in a serum sample from the said individual, selecting a method-specific reference value and cut-off value for respective analyte, assessing the topography and phenotype of gastritis based on a comparison of the pepsinogen I and gastrin-17 concentrations so determined with their respective method-specific reference and cut-off values, and correlating the so assessed gastritis phenotype with the risk for peptic ulcer. Preferably also *Helicobacter* antibodies are determined in the sample.

10 Claims, 2 Drawing Sheets

Figure 1:
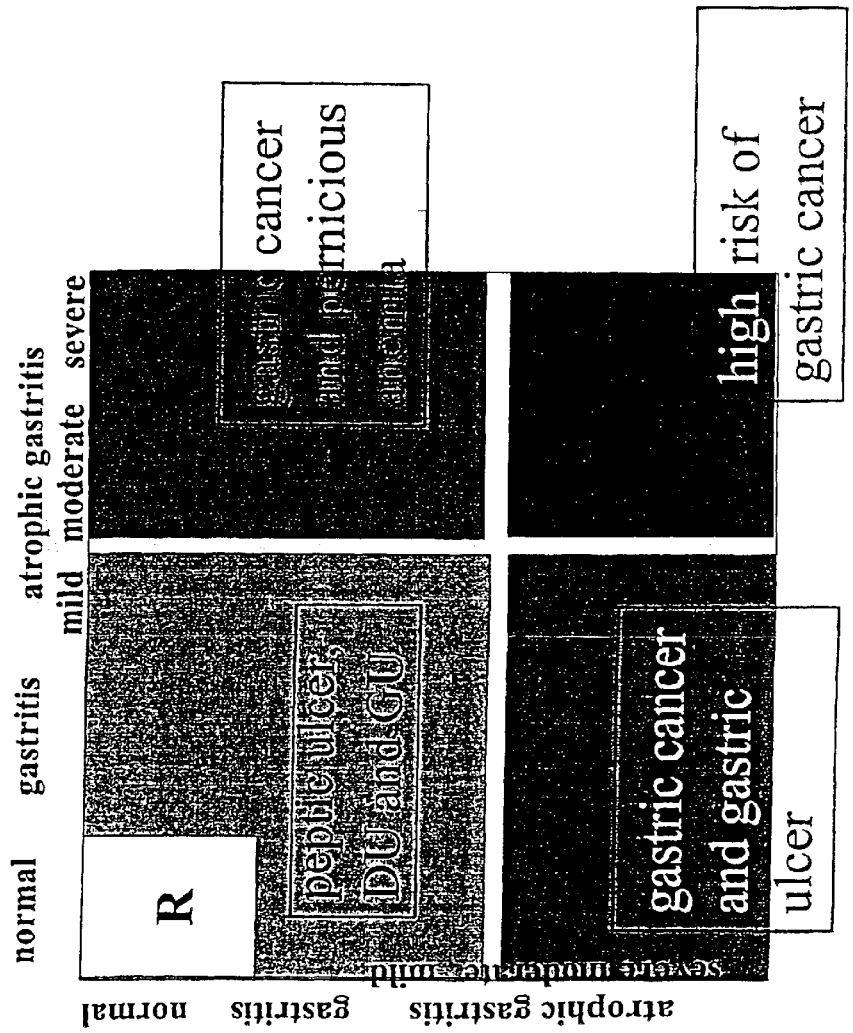

TOPOGRAPHIC PHENOTYPES OF CHRONIC GASTRITIS
AND THE RISK OF GASTRIC DISEASES

OTHER PUBLICATIONS

Kekki, M et al, Scan Journal of Gastroenterology, vol. 26 (suppl. 186), pp. 109–116, 1991, Serum pepsinogen–I and Serum Gastrin in the screening of Severe atrophic corpus gastritis.*

Malfertheiner, P et al, Eur. J. Gastroenterol. Hepatol., 1993, vol. 5(suppl. 1), pp. S1–S8, *Helicobacter pylori* and the pathogenesis of duodenal ulcer disease.*

Mulholland, G et al, Gut (England), Jun. 1993, vol. 34(6), pp. 757–761, *Helicobacter pylori* related hypergastinaemia is the result of a selective increase in gastrin–17.*

Petersen, B et al, Scand. J. Gastroenterol., vol. 18(5), pp. 635–642, Increased concentrations of the amino terminal fragment of gastrin–17 in acute duodenal ulcer and acute gastritis.*

Petersen,B, Scand. J. Gastroenterol.(Norway), 1983, vol. 18(5), pp. 613–617, Metabolism of the NH2–terminal tridecapeptide of gastrin–17 in normal subjects and duodenal ulcer patients.*

Pilotto, A et al, J. Am. Geriatr. Soc., vol. 44, pp. 665–670, 1996.*

Plebani, M, Crit. Rev. Clin. Lab. Sci, 1993, vol. 30(3), pp. 273–328, Pepsinogens in health and Disease.*

Walker, K et al, Clin. Ther. vol. 7(6), pp. 704–716, 1985.*

Westerveld, BD et al, Cancer, Mar. 1, 1987, Vo.l. 59(5), pp. 952–958.*

Westerveld, BD et al, Prog. Clin. Biol. Res., 1985, vol. 173, pp. 201–212.*

Valle, J et al, Eur. J. of Gastroenterol. and Hepatol., vol. 4 (12), pp. 985–989, 1992.*

Wu, M–S et al, Am. J. of Gastroenterology, vol. 89(8), p. 1361, 1994, abstract No. 304, (abstract only).*

Roll, J et al, Arch Intern. Med. vol. 157, May 12, 1997, pp. 994–998, Diagnosis and Treatment of *Helicobacter pylori* infection among California Medicare Patients.*

The American Journal of Gastroenterology, vol. 89, No 9, 1994, Tseng–Shing Chen, M.D. et al, "effect of Eradiction of *Helicobacter pylori* on Serum Pepsinogen I, Gastrin, and Insulin in Duodenal Ulcer Patients: A 12–month Follow–up Study" p. 1511–p. 1514.

European Journal of Gastroenterology & Hepatology, vol. 11, 1999, Javier P. Gisbert et al, "Basal and stimulated gastrin and pepsinogen levels after eradicaion of *Helicobacter pylori*: a 1–year follow–up study" p. 189–p. 200.

* cited by examiner

METHOD FOR ASSESSING THE RISK OF PEPTIC ULCER, COMPRISING THE STEPS OF DETERMINING QUANTITATIVELY THE CONCENTRATIONS OF PEPSINOGEN I (PGI) AND GASTRIN-17 IN A SERUM SAMPLE

This application is the national phase under 35 U.S.C. § 371 of PCT International Application No. PCT/FI00/00377 which has an International filing date of Apr. 28, 2000, which designated the United States of America and was published in English.

This invention relates to a method for assessing the risk of peptic ulcer by determining the presence and topographic phenotype of gastritis in an individual.

Chronic gastritis is an extremely common disorder. It is estimated that nearly half of the world's population will get gastritis during their lifetime. Chronic gastritis is most often caused by *Helicobacter pylori* infection and can be considered an immunological reaction against this bacterium in a great majority of cases [1–6].

Chronic gastritis is a rather unique bacterial infection with characteristic chronicity and life-long duration. A spontaneous healing of gastritis, normalization of the gastric mucosa in both antrum and corpus, is a rare event. Usually the natural course of chronic gastritis is a sequence of alterations from inflammation to atrophy which significantly changes the structure and function of the gastric mucosa. The outcome of chronic gastritis represents several important disorders, all of which seem to show an association with a specific alteration and with some particular state in the course of gastritis.

Bacterial infection results in simple inflammation which consists of immunocompetent lymphocytes and plasma cells, and often granulocytes, in the gastric mucosa [7–11]. Studies in children and young people suggest that this chronic inflammation is the prevailing initial phenotype of gastritis in early age. In the elderly, atrophy and intestinal metaplasia of the underlying mucosa are common phenomena and increase in prevalence with age [12–18].

Studies suggest a slow progression of chronic gastritis into atrophy. Gastritis and subsequent atrophy are important causes of several functional and homeostatic impairments of the gastric mucosa. Atrophy results in failure of the secrection of acid, pepsinogens and gastrin from the corpus and antral mucosa along with the development of atrophy (loss of normal mucosal glands).

*Helicobacter pylori* infection and gastritis are important risk factors for peptic ulcer, both duodenal and gastric. Gastritis precedes both duodenal and gastric ulcer suggesting a causal relationship between *H. pylori* infection, gastritis and ulcer formation [19,20]. Antral gastritis (inflammation limited to antrum) or pangastritis (inflammation of both antrum and corpus) increase the risk for duodenal ulcer approximately 10-fold [19]. Antral or pangastritis with coexisting antral atrophy may increase the risk of gastric ulcer in particular, both in cumulative and relative terms, several tens of times compared with the risk in people with a normal stomach [21, 22].

Gastritis may also decrease the risk of ulcers. This is especially the case when gastritis occurs in the corpus and progresses into marked atrophy. Irrespective of the presence and grade of lesions in the antrum, the risk of peptic ulcer is decreased to a level which is even lower than that in people with a normal stomach.

In general, the risk of peptic ulcer increases exponentially with an increasing grade of antral lesions (gastritis and atrophy), but decreases exponentially with an increasing grade of lesions in the corpus.

It is possible to electrophoretically distinguish 7 different pepsinogens from the gastric mucosa in humans. Of these the five fastest form the immunologically uniform group of pepsinogen I. The other two form the pepsinogen II group. The group I pepsinogens are synthezised only in the main cells and the mucous secreting cells of the corpus area of the stomach. In contrast thereto, group II pepsinogens are formed in the glands over the whole stomach area and to some degree also in the upper part of the duodenum in the Brunner's glands. In the serum of a healthy person the pepsinogen I concentration is approximately 6 times that of the pepsinogen II concentration. In atrophic gastritis of the corpus area of the stomach the serum pepsinogen I concentration decreases, whereas the serum pepsinogen II concentration remains at the previous level. Thus, the serum pepsinogen I concentration fairly well reflects the number of pepsinogen secreting cells in the corpus area of the stomach, and their condition. The more serious the atrophic gastritis of the corpus area of the stomach is, the lower is the serum pepsinogen I concentration. A low pepsinogen I concentration in the serum indicates severe atrophic corpus gastritis with a sensitivity of over 90% and a specificity of almost 100% [23].

Gastrin is secreted in the gastrointestinal tract in at least three different forms, the immunoreactive activity of all these forms being measured when serum gastrin is determined (total serum gastrin). Gastrin subtypes are the so-called minigastrin (G-14), little gastrin (G-17) and big gastrin (G-34). Physiologically most important are gastrin-17 and gastrin-34. The effect of gastrin-17 on the secretion of hydrochloric acid is 6 times that of gastrin-34. Gastrin is secreted from the so-called G-cells, which appear both in antrum and in duodenum. The most important accelerators of gastrin secretion is the tonus of the vagus nerve and the protein degradation products. The secretion of gastrin is slowed down by a pH decrease of below 2.5. The gastrin secreted from the antrum is to over 90% of the gastrin-17 type, whereas the duodenal gastrin is primarily of the gastrin-34 type [24]. In a fasting situation, primarily gastrin-34 is found in the serum, whereas after a meal the serum gastrin is of the gastrin-17 type [25]. The secretion of gastrin-17 can also be studied using the so-called protein stimulation test. In such a test, a blood sample after fasting is taken in the morning, whereafter the patient eats a protein rich standard meal and blood samples are taken at 15 minute intervals for two hours. The maximal increase is evident after appr. 20 minutes.

In atrophic antrum gastritis the mucous membrane of the antrum is atrophied and thus its gastrin-17 secretion decreases and its concentration in the serum is reduced. A reduced gastrin-17 concentration in the serum would thus be an indicator of antrum atrophy and of an increased risk of cancer in this area. In case the mucous membrane of the antrum is atrophied, there is a reduced response also in the protein stimulation test, which seems to be a more sensitive indicator of atrophy than the mere concentration determination. In the publication WO 96/15456, there is described a method for screening for the risk of cancer, by determining atrophy in the various parts of the stomach.

Due to the high prevalence of chronic gastritis especially in the elderly population, it would, however, be of importance to develop a method also for assessing the presence of and topographic phenotypes of chronic gastritis in order to assess the risk for peptic ulcer associated therewith. Especially it would be beneficial to develop a method which would allow the said assessment to be carried out in a non-invasive manner, that is, without having to resort to biopsy sampling of the mucosa during diagnostic gastroscopy. It would also be advantageous to develop a method which would allow not only an assessment of the risk of peptic ulcer, but a method which would allow the differentiation between the risk of gastric ulcer and that of duodenal ulcer.

The above mentioned objects are achieved with the method according to the invention, which concerns a method for assessing the risk of peptic ulcer in an indivdual, the method comprising the steps of determining quantitatively the pepsinogen I and gastrin-17 concentrations in a serum sample from the said indivdual, selecting a method-specific reference value and cut-off value for respective analytes, comparing the pepsinogen I and gastrin-17 concentrations so determined with their respective method-specific reference value and cut-off value, whereby a serum pepsinogen I and gastrin-17 concentration above the upper limit of respective reference value, or a serum pepsinogen I concentration above the upper limit of its reference value in combination with a gastrin-17 concentration within the reference range or below its cut-off value, indicates an increased risk of peptic ulcer in said individual.

The present invention thus includes a step of identifying an individual having either a serum pepsinogen I and gastrin-17 concentration above the upper limit of respective reference value, or a serum pepsinogen I concentration above the upper limit of its reference value in combination with a gastrin-17 concentration within the reference range or below its cut-off value, as being an individual with an increased risk of, or having a predisposition for, peptic ulcer.

According to a preferred embodiment of the invention, the method includes a step of diagnosing said individual also for *Helicobacter pylori* infection by determining *Helicobacter pylori* antibodies in the serum sample.

The method according to the invention thus uses in combination, two or preferably three determinations from a serum sample of a patient to be screened for the risk of peptic ulcer, namely a determination of serum pepsinogen I (PGI), gastrin-17, (G-17) and optionally also *Helicobacter pylori* antibodies.

The different methods for the determination of the PGI, G-17 and *Helico* antibodies are as such well known to the person skilled in the art, and there are also kits commercially available for carrying out the determinations. Such methods are usually immunological methods, using mono- or polyclonal antibodies to the analytes. The detection methods for use include, for example, measuring absorbance, fluorescence or luminescence. It is also possible to carry out all the three measurements simultaneously, for example on the same microplate, in different wells thereon, which combined assay system provides for an especially convenient method of diagnosis.

The invention includes a step of comparing the measured analyte concentrations, to method-specific cut-off and reference values for said analytes. The selection of such values is well known to a person skilled in the art, and depends on the specificity and sensitivity chosen for the test method used for the determination of the analyte concentrations, see e.g. William J Marshall, Clinical Chemistry, Third Edition, 1995, Mosby.

For the determination of *Helicobacter pylori* antibodies, a number of commercial "kits" are available (e.g. Orion Pyloriset EIA-G, Pyloriset EIA-A, EIA 2G by Roche, Pyloristat by Whittaker Bioproducts). Antigens can be prepared from *Helicobacter pylori* bacteria in various ways [26] and they are also commercially available.

Figure 2:
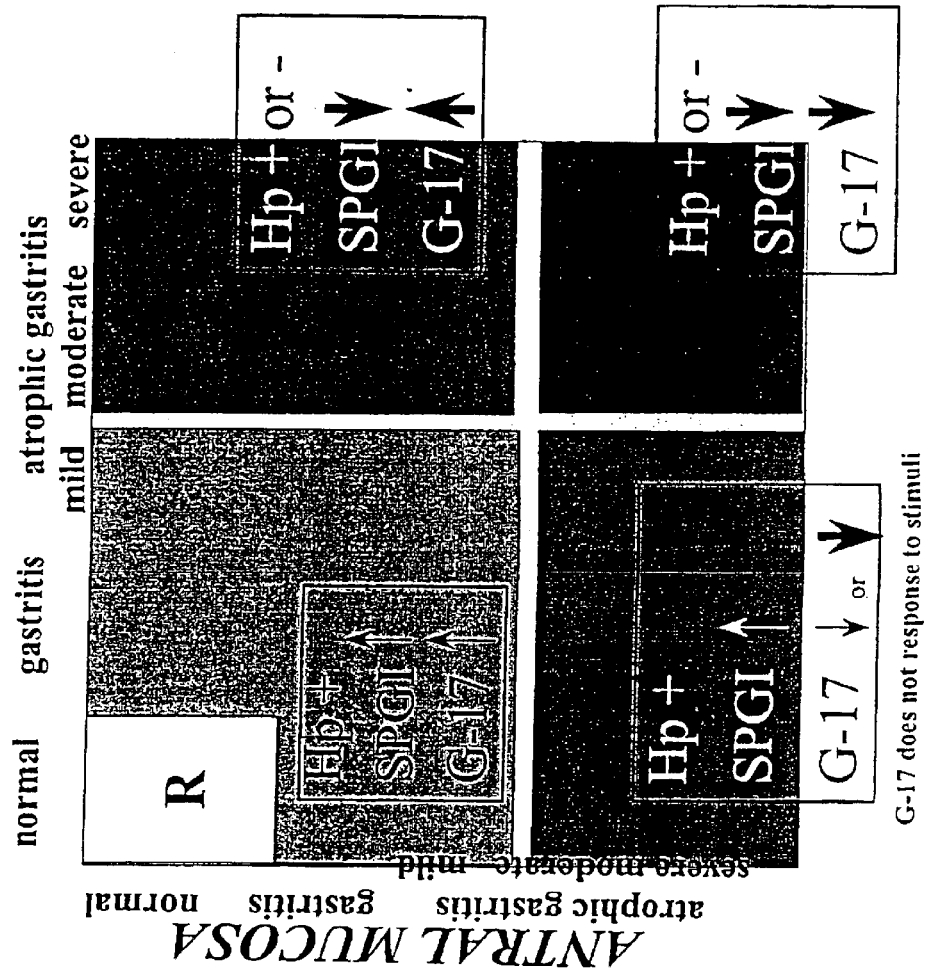

In the appended drawing,

FIG. 1 illustrates the topographic phenotypes of chronic gastritis and associated risk for gastric disease, and FIG. 2 illustrates the association between serological tests for SPGI, G-17 and *Helicobacter pylori* infection and the topographic phenotypes of chronic gastritis.

In the invention, the term "topography" or "topographic" as used, refers to the location of the gastritis in the stomach. In both corpus and antrum mucosa, one distinguishes between the phenotypes: normal, gastritis (superficial gastritis) and atrophic gastritis, which atrophic gastritis in turn is classified, in order of severity, in mild, moderate and severe atrophic gastritis.

As is evident from the FIG. 1, there is an increased risk (as compared to individuals with a healthy stomach, marked R in the Figures) for gastric and especially for duodenal ulcer when the gastritis on both the corpus and antrum mucosa is of superficial or mild atrophic phenotype, the risk increasing especially with increasing severity of antral gastritis. In this case both the serum pepsinogen I and the gastrin-17 concentrations are increased over their reference values, the upper reference limit being, depending on the specificity and sensitivity agreed upon for the method in question, 25–120 µg/l for PGI. Also the gastrin-17 will be above its normal or reference values, which are in the range of 2–25 pmol/l. For the *Helicobacter pylori* positiveness, the cut-off titer is 200–500.

In a situation where the corpus is normal or the gastritis in the corpus is of superficial phenotype and that of the antrum is of moderate to severe atrophic phenotype, there is an increased risk especially for gastric ulcer (as well as gastric cancer). In this situation, the pepsinogen I concentration is still above the upper limit of its reference value, as indicated above, but the gastrin-17 value is at normal range, at its lower reference value, or below its cut-off value for severe atrophy, which depending on the specificity and sensitivity of the method is 0.1–2 pmol/l. This method can be combined with a protein stimulation test, by measuring the gastrin-17 concentration in the serum at the base line situation and then after protein stimulation, for example after a protein rich standard meal. A lack of response in this test supports the risk of gastric ulcer.

It can also be seen from the Figures that at increasing severity of atrophic corpus gastritis, with no or only superficial antrum gastritis, the serum pepsinogen I concentration falls below the cut-off value indicating an increased risk i.a. for cancer and pernicious anaemia, which cut-off value, depending on the specificity and sensitivity of the chosen method, is 20–30 µg/l. The gastrin-17 concentration is still above its reference value as indicated above.

At increasing severity of both antral and corpus atrophic gastritis, the serum pepsinogen I concentration is below its cut-off value indicating an increased risk of cancer, and the serum gastrin-17 concentration is at its lower reference limit, or below its cut-off value indicating an increased risk of cancer. These gastritis phenotypes are associated with a very high risk of gastric cancer.

The use of the combination method for assessing gastritis phenotypes of the mucosa in the various parts of the stomach as described above, is shown in the Table 1.

Table 1. Combination method for serum pepsinogen I and gastrin-17 for assessing phenotypes of gastritis of the mucosa of the corpus area or the antrum area of the stomach.

TABLE 1

| Topography & Phenotype | | CORPUS | | |
|---|---|---|---|---|
| | | 1-3 | 4-5 | Assay |
| A | 1- | > upper ref. limit | < cut-off value | SPG1 |
| N | 3 | > upper ref. limit | >> upper ref. limit | SG-17 |
| T | | (+) | (+)/(−) | Helico |
| R | 4- | > upper ref. limit | < cut-off value | SPGI |
| U | 4 | normal or ≤ cut-off value | < cut-off value | SG-17 |
| M | | (+) | (−) | Helico | phenotype:
1 = normal, 2 = superficial gastritis, 3 = mild, 4 = moderate, 5 = severe atrophic gastritis
SPGI = serum pepsinogen I
SG-17 = serum gastrin-17

References

1. MARSHALL, B J, WARREN J R: Unidentified curved bacilli in the stomach of patients with gastritis and peptic ulceration. *Lancet* 1984, i:1311–1314.
2. GOODWIN C S: The Sydney System: microbial gastritis. *J. Gastroenterol Hepatol* 1991, 6:235–237.
3. DIXON M F: *Helicobacter pylori* and peptic ulceration; histopathological aspects. *J. Gastroenterol Hepatol* 1991, 6:125–130.
4. RAUWS E A J, LANGENBERG W, HOUTHOFF H J ZANEN H C, TYTGAT G N J: *Campylobacter pyloridis*-associated chronic active antral gastritis, *Gastroenterology* 1988, 94:33–40.
5. SIURALA M, SIPPONEN P, KEKKI M: *Campylobacter pylori* in a sample of Finnish population: relation to morphology and functions of the gastric mucosa. *Gut* 1988, 29:909–916.
6. PRICE A B, LEVI J, DOLBY J M, DUNSCOMBE P L, SMITH A, CLARK J, ET AL: *Campylobacter pyloridis* in peptic ulcer disease; microbiology, pathology and scanning electron microscopy. *Gut* 1985, 26:1183–1188.
7. MISIEWICZ J J: The Sydney System: a new classification of gastritis. Introduction. *J. Gastroenterol Hepatol* 1991, 6:207–208.
8. PRICE Ab: The Sydney System: histological division. *J Gastroenterol Hepatol* 1991, 6:209–222.
9. WHITEHEAD R, TRUELOVE S C, GEAR M W L: The histological diagnosis of chronic gastritis in fiberoptic gastroscope biopsy specimens. *J Clin Pathol* 1972, 25:1–11.
10. CORREA P: Chronic gastritis: a clinico-pathological classification *Am J Gastroenterol* 1988, 83:504–509.
11. YARDLEY, J H. Pathology of chronic gastritis and duodenitis. In *Gastroeintestinal Pathology* edited by Goldman H, Appelman H D, Kauffman N Baltimore: Williams and Wilkins, 1990, pp. 69–143.
12. SIURALA M, SIPPONEN P, KEKKI M: Chronic gastritis: dynamic and clinical aspects. *Scand J Gastroenterol* 1985, 20 (suppl 109):69–76.
13. SIURALA M, VARIS K, KEKKI M: New aspects on epidemiology, genetics, and dynamics of chronic gastritis. *Front Gastrointest Res* 1980, 6:148–165.
14. CHELI R, SANTI I, CIANCAMERA G, CANCIANI G: A clinical and statistical follow-up of atrophic gastritis. *Am J Dig Dis* 1973, 18:1061–1066.
15. CHELI R, PERASSO A, GIACOSA A: Gastritis, Berlin: Springer Verlag, 1987.
16. SIPPONEN P, KEKKI M, SIURALA M: Age-related trends of gastritis and intestinal metaplasia in gastric carcinoma patients and in controls representing the population at large. *Br J Cancer* 1984, 49:521–530.
17. VILLAKO K, SIURALA M: The behaviour of gastritis and related conditions in different population samples. *Ann Clin Res* 1981, 13:114–118.
18. CHELI R, SIMON L, ASTE H, FIGUS I A, NIGOLD G, BAJTAI A, ET AL: Atrophic gastritis and intestinal metaplasia in asymptomatic 4Hungarian and Italian population. *Endoscopy* 1980, 12:105–108.
19. SIPPONEN P: Chronic gastritis and ulcer risk. *Scand J Gastroenterol* 1990, 25:193–196.
20. SIPPONEN P, AARYNEN M, KAARIAINEN I, KETTUNEN P, HELSKE T, SEPPALA K: Chronic antral gastritis, Lewis a+ phenotype and male sex in predicting coexisting duodenal ulcer. *Scand J Gastroenterol* 1989, 24:581–588.
21. SIPPONEN P, SEPPALA K, AARYNEN M, HELSKE T, KETTUNEN P: Chronic gastritis and gastroduodenal ulcer: a case control study on risk of coexisting duodenal and gastric ulcer in patients with gastritis. *Gut* 1989, 30:922–929.
22. SIPPONEN P, VARIS K, FRAKIG O, KORRI U -M, SEPPALA K, SIURALA M: Cumulative 10-year risk of symptomatic duodenal and gastric ulcer in patients with or without gastritis. A clinical follow-up of 454 patients. *Scand. J Gastroenterol* 1990, 25:966–973.
23. VARIS K, KEKKI M, HÄRKÖNEN M, SIPPONEN P & SAMLOFF I M 1991: Serum pepsinogen I and serum gastrin in the screening of atrophic pangastritis with high risk of gastric cancer. Scand J Gastroenterology 26 (suppl 186): 117–123.
24. BERSON S A & YALOW R S, (1971): Nature of immunoreactive gastrin extracted from tissues of gastrointestinal tract. Gastroenterology 60:215–222.
25. LAMERS C, HARRISON A, IPPOLITI A & WALSH J (1979): Molecular forms of circulating gastrin in normal subjects and duodenal ulcer patients. Gastroenterology 76: 1179.
26. LELWALA-GURUGE J, NILSSON I, JUNGH A & WADSTRÖM T (1992): Cell surface proteins of *Helicobacter pylori* as antigens in an ELISA and a comparison with three commercial ELISA. Scand J Infect Dis 24:457–465.

What is claimed is:

1. A method for assessing the risk of duodenal ulcer comprising
   a) obtaining a serum sample from a patient;
   b) quantitatively measuring the pepsinogen I from said serum sample using an immunoassay and comparing the value obtained to a reference range of 25–125 μg/l for pepsinogen I; and
   c) quantitatively measuring the gastrin-17 from said serum sample using an immunoassay and comparing the value obtained to a reference range of 2–25 pmol/l, whereby a pepsinogen I concentration in said serum sample above the upper limit of the pepsingogen I reference range and a gastrin-17 concentration above the upper limit of the gastrin-17 reference range is indicative of an increased risk of duodenal ulcer.

2. A method for assessing the risk of gastric ulcer comprising
   a. obtaining a serum sample from a patient;
   b. quantitatively measuring the pepsinogen I from said serum sample using an immunoassay and comparing the value obtained to a method-specific reference range of 25–125 μg/l for pepsinogen I; and c. quantitatively measuring the gastrin-17 from said serum sample using an immunoassay and comparing the value obtained to a gastrin-17 cut-off value of 0.1–2 pmol/l, which overlaps the lower end of the reference range of 2–25 pmol/l for gastrin-17, whereby a pepsinogen I concentration in said serum sample above the upper limit of the pepsinogen I reference range and a gastrin-17 concentration within the gastrin-17 reference range or below the gastrin-17 cut-off value is indicative of an increased risk of gastric ulcer.

3. The method according to the claim 1 or 2, further comprising conducting an immunoassay to detect the presence of *Helicobacter pylori* antibodies.

4. The method according to claim 1 or 2, further comprising a protein stimulation test that measures serum gastrin-17 concentration after fasting and then after a protein rich standard meal.

5. The method according to claim 4, wherein no change in the serum gastrin-17 concentration after a protein rich meal as compared with the value after fasting is indicative of a risk of gastric ulcer.

6. The method according to the claim 1 or 2, wherein said pepsinogen I or gastrin-17 immunoassay is conducted on a plastic, glass or cellulose support.

7. The method according to the claim 6, wherein said plastic, glass or cellulose support is a microplate.

8. The method according to claim 1 or 2, wherein said immunoassay is conducted with an enzyme labeled antibody and absorbance, fluorescence or luminescence is measured.

9. The method according to claim 1 or 2, wherein said pepsinogen I immunoassay is performed using a polyclonal or monoclonal antibody, which specifically binds to said pepsinogen I.

10. The method according to claim 1 or 2, wherein said gastrin-17 immunoassay is performed using a polyclonal or monoclonal antibody, which specifically binds to said gaatrin-17.

* * * * *